US012599759B2

(12) United States Patent
Huang et al.

(10) Patent No.: US 12,599,759 B2
(45) Date of Patent: Apr. 14, 2026

(54) NON-IMPLANTABLE TRAINING METHOD FOR TRAINING GENIOGLOSSUS MUSCLE STRENGTH

(71) Applicant: METAL INDUSTRIES RESEARCH & DEVELOPMENT CENTRE, Kaohsiung (TW)

(72) Inventors: Bol-Wei Huang, Kaohsiung (TW); Yu-Sheng Lin, Kaohsiung (TW); Tung-Lin Tsai, Tainan (TW); Chun-Chieh Tseng, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 319 days.

(21) Appl. No.: 18/457,042

(22) Filed: Aug. 28, 2023

(65) Prior Publication Data

US 2025/0073451 A1     Mar. 6, 2025

(51) Int. Cl.
*A61N 1/04*          (2006.01)
*A61N 1/36*          (2006.01)

(52) U.S. Cl.
CPC ......... *A61N 1/0452* (2013.01); *A61N 1/0496* (2013.01); *A61N 1/36034* (2017.08)

(58) Field of Classification Search
None
See application file for complete search history.

(56) References Cited

U.S. PATENT DOCUMENTS

| 11,033,738 | B2 | 6/2021 | Steier | |
| 2011/0230702 | A1* | 9/2011 | Honour | A61N 1/40 |
| | | | | 607/42 |
| 2017/0007173 | A1* | 1/2017 | Adamczyk | A61B 5/4812 |
| 2017/0209695 | A1* | 7/2017 | Solomon | A61N 7/02 |
| 2020/0121921 | A1* | 4/2020 | Sama | A61N 1/3603 |

FOREIGN PATENT DOCUMENTS

| JP | 2016134778 A | 7/2016 |
| JP | 2018504243 A | 2/2018 |
| JP | 2022505305 A | 1/2022 |

* cited by examiner

*Primary Examiner* — Michael W Kahelin
(74) *Attorney, Agent, or Firm* — WPAT, PC

(57) ABSTRACT

An in vitro training method for training genioglossus muscle strength includes adhering an electrode patch of an in vitro training device to a bottom of a chin of a user during a non-sleep period. The electrode patch receives an electrical stimulation signal from an electrical stimulation module of the in vitro training device to stimulate the genioglossus muscle of the user through transdermal electrical stimulation. The electrode patch includes a body surface adhering face and an assembling face opposite to the body surface adhering face. The body surface adhering face is adhered to the bottom of the chin of the user to align with the genioglossus muscle. The electrical stimulation module is disposed on the assembling face and in electrical connection with the electrode patch. The electrical stimulation module sends an electrical stimulation signal to stimulate the genioglossus muscle through transdermal electrical stimulation.

1 Claim, 4 Drawing Sheets

2

T

1    M

NON-IMPLANTABLE TRAINING METHOD FOR TRAINING GENIOGLOSSUS MUSCLE STRENGTH

BACKGROUND OF THE INVENTION

1. Field of the Invention

The present invention relates to an in vitro training method and an in vitro device for training muscle strength and, more particularly, to an in vitro training method and an in vitro training device used for training the genioglossus muscle strength during a non-sleep period.

2. Description of the Related Art

According to the investigation by the World Health Organization (WHO), up to one billion of adults (aged 30-69) suffer from obstructive sleep apnea (OSA), including 42 millions of OSA patients in the U.S., among which one in every five adults suffers from mild OSA, and one in every fifteen adults suffers from severe OSA. Furthermore, according to the statistics of the Taiwan Society of Sleep Medicine (TSSM), about 450,000 people in Taiwan have poor sleep quality due to apnea.

The major causes of sleep apnea include a narrow airway which is inherent or caused by obesity, or an airway blockage resulting from collapse which tends to occur due to insufficient muscle tension in the airway of an aged body. The types of blockage causing sleep apnea include nasal cavity blockage, soft palate blockage in the oral cavity, and tongue root blockage. About 70% of the patients (about 0.65 billions of people in the world, including at least 300,000 people in Taiwan) belong to the tongue root blockage type which is the most common. The tongue root blockage is strongly relevant to reduction in actuation of upper airway muscles and weakened activation of infrahyoid muscles. OSA patients not only snore (which adversely affects the sleep quality of the person sleeping nearby) but also have poor sleep quality, leading to drowsiness in the daytime and reduced concentration and, in severe cases, may even cause sudden death due to apnea during the sleep period.

However, medicines for treating sleep apnea are not available currently. Common conventional methods for improving sleep apnea include: (1) using a mandibular advancement device which is suitable for mild and moderate sleep apnea patients, but the patients are difficult to sleep due to a sensation of a foreign body in the oral cavity caused by the mandibular advancement device; (2) instrument therapy: for example, wearing a continuous positive airway pressure (CPAP) on the face of a patient during sleep, thereby continuously filling air into the airway and, thus, expanding the airway, but the CPAP instrument is bulky and expensive; (3) surgical treatment: for example, cutting the uvula or the tonsil to enlarge the airway, or implanting an electrical stimulation device to electrically stimulate the genioglossus muscle and other muscles of the upper airway during sleep to thereby increase the muscle tension of the upper airway muscles. As for mild and moderate sleep apnea patients who are difficult to accept or withstand the CPAP therapy, surgical implantation of an electrical stimulation device is considered. However, the operation involves infection risks, and removal of the device and re-implantation are required when the device malfunctions, and the electrical stimulation during sleep will adversely affect the sleep quality of the patient.

Thus, it is necessary to improve the conventional methods for improving sleep apnea.

SUMMARY OF THE INVENTION

To solve the above problems, it is an objective of the present invention to provide an in vitro training method for training genioglossus muscle strength, in which transdermal electrical stimulation is conducted during a non-sleep period to stimulate the genioglossus muscle for restoring the muscular tension through training, which avoids the operational risks of implantation and discomfort during the sleep period.

It is another objective of the present invention to provide an in vitro training device for training genioglossus muscle strength for carrying out the above method.

It is a further objective of the present invention to provide an in vitro training device for training genioglossus muscle strength, which is easy to use and carry.

As used herein, the term "a", "an" or "one" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

As used herein, the term "engagement", "coupling", "assembly", or similar terms is used to include separation of connected members without destroying the members after connection or inseparable connection of the members after connection. A person having ordinary skill in the art would be able to select according to desired demands in the material or assembly of the members to be connected.

An in vitro training method for training genioglossus muscle strength according to the present invention includes adhering an electrode patch of an in vitro training device to a bottom of a chin of a user during a non-sleep period. The electrode patch receives an electrical stimulation signal from an electrical stimulation module to stimulate the genioglossus muscle of the user through transdermal electrical stimulation. The electrical stimulation signal has a voltage of 1-100 V, an electric current of 1-30 mA, a pulse width of 1-500 ms, and a frequency of 1-80 Hz.

Therefore, by the in vitro training method for training genioglossus muscle strength, transdermal electrical stimulation is conducted during a non-sleep period to stimulate the genioglossus muscle for restoring the muscular tension through training, which avoids the operational risks of implantation and discomfort during the sleep period. Thus, there are no operational risks, and the sleep quality is not adversely affected. Furthermore, the user may proceed with the electrical stimulation training at any convenient time and place, which can effectively increase the training convenience and comfort for the user, thereby increasing the user's intention of continuous use as well as the training effect.

In an example, the in vitro training method is preferably carried out once a day and preferably not more than one hour every time.

In an example, the in vitro training method may be carried out plural times a day, and the interval between two training times is at least one hour.

Furthermore, the present invention further provides an in vitro training device for training genioglossus muscle strength. The in vitro training device includes an electrode patch and an electrical stimulation module. The electrode patch includes a body surface adhering face and an assembling face opposite to the body surface adhering face. The body surface adhering face is configured to be adhered to a bottom of a chin of a user to align with a genioglossus muscle of the user. The electrical stimulation module is disposed on the assembling face and in electrical connection with the electrode patch. The electrical stimulation module is configured to send an electrical stimulation signal to stimulate the genioglossus muscle of the user through transdermal electrical stimulation. Therefore, aside from carrying out the above in vitro training method to improve the sleep apnea, the electrical stimulation module of the in vitro training device can be directly connected to the electrode patch without wires disposed therebetween, such that the whole device can be more compact and tidy and easier to use, carry, and maintain.

In an example, preferably, the body surface adhering face can be repeatedly adhered to and removed from a skin of the user. Therefore, the user can repeatedly use the same electrode patch, increasing the use efficiency of material.

In an example, the assembling face of the electrode patch may include at least one first electrical connecting portion. The electrical stimulation module may include a casing, at least one power source disposed in the casing, and at least one second electrical connecting portion in electrical connection with the at least one power source and located outside of the casing. The electrical stimulation module is preferably detachably coupled with the electrode patch. The casing may cover a portion of the assembling face. The at least one second electrical connecting portion may be in electrical connection with the at least one first electrical connecting portion. Therefore, replacement of the electrode patch is more convenient.

In an example, the electrical stimulation module may include a control unit located in the casing. The at least one power source may be in electrical connection with the control unit. The control unit may be configured to control the electrical stimulation signal sent to the electrode patch. Therefore, the structure of the in vitro training device can be simplified.

In an example, the control unit may be coupled with an intelligent device and may be configured to adjust a stimulation intensity and/or a frequency of the electrical stimulation signal through an application interface of the intelligent device. Therefore, the user can adjust the electrical stimulation effect according to needs and comfort at any time, thereby increasing the training effect and the training comfort experience.

In an example, the electrical stimulation signal may have a voltage adjustment range of 0-100 V, an electric current adjustment range of 0-30 mA, a pulse width adjustment range of 1-500 ms, and a frequency adjustment range of 1-80 Hz. Therefore, the user may start, adjust, pause, or stop the electrical stimulation according to needs, which improves the operational convenience and assures the use safety and the training effect.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
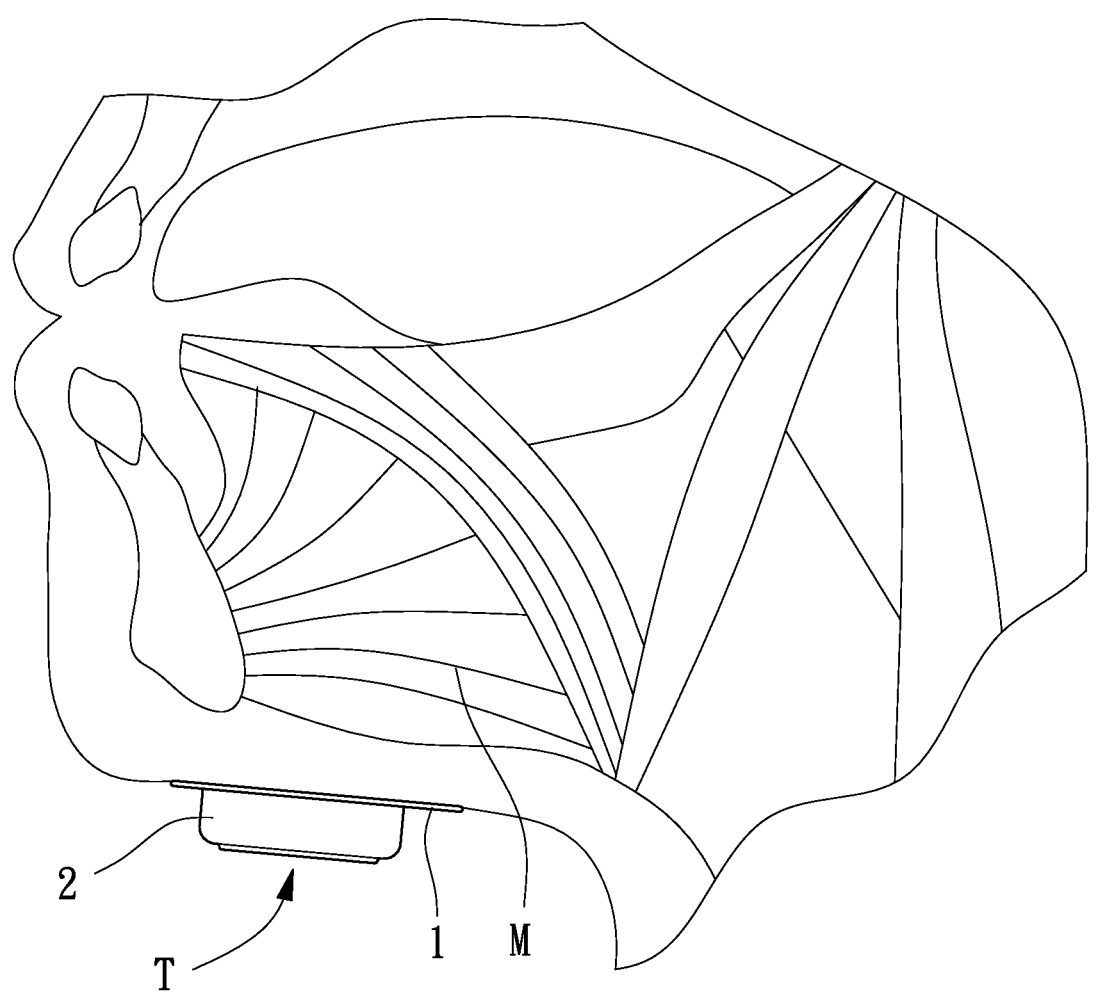
FIG. 1 a schematic view illustrating use of an in vitro training method according to the present invention.

When the terms "front", "rear", "left", "right", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

DETAILED DESCRIPTION OF THE INVENTION

With reference to FIG. 1, the present invention provides an in vitro training method for training genioglossus muscle strength. The method includes adhering an electrode patch 1 of an in vitro training device T to a bottom of a chin of a user during a non-sleep period. The electrode patch 1 receives an electrical stimulation signal from an electrical stimulation module 2 to stimulate the genioglossus muscle M of the user through transdermal electrical stimulation. The electrical stimulation signal has a voltage of 1-100 V, an electric current of 1-30 mA, a pulse width of 1-500 ms, and a frequency of 1-80 Hz. These parameters can be adjusted by a doctor according to professional judgement and the conditions of the patient, such as the personal demands of the patient (e.g., the thickness of the genioglossus muscle M or the electrical resistance of the feedback of the electrical stimulation). In this way, the genioglossus muscle can be trained effectively and safely.

Therefore, the in vitro training method according to the present invention may be carried out during the non-sleep period, e.g., 30 minutes before sleep. The muscle endurance of the genioglossus muscle M of the user can be trained through transdermal electrical stimulation. A supporting force of the genioglossus muscle M can also be trained and the original muscle tension of the genioglossus muscle M can be restored. Thus, the blockage of the airway due to sinking of the tongue during the sleep period can be improved, thereby improving the symptoms of sleep apnea. The in vitro training method may be preferably carried out once a day and preferably not more than one hour every time. In a case that the in vitro training method should be carried out plural times a day, the interval between two training times should be at least one hour.

Figure 2:
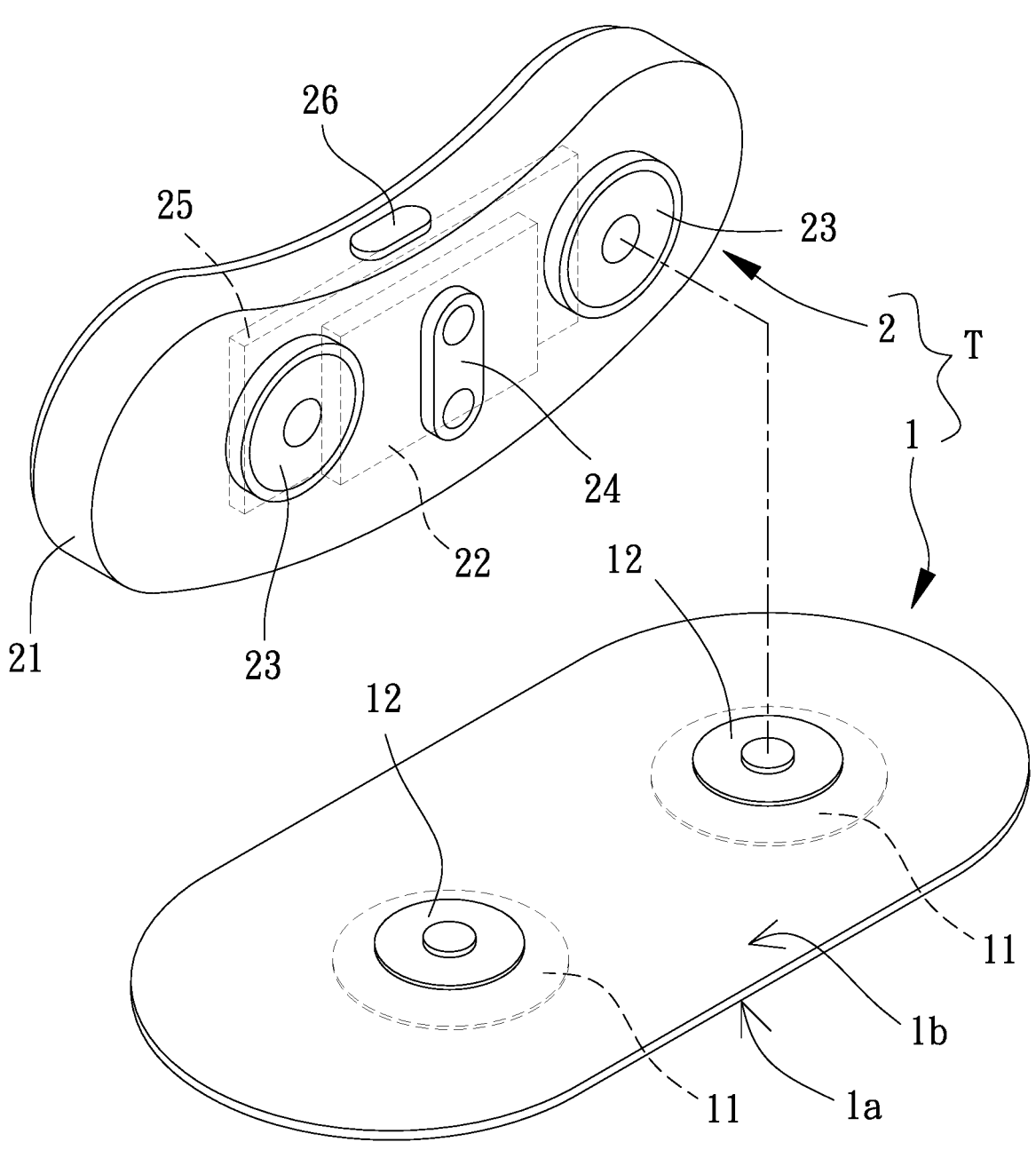
FIG. 2 is an exploded, perspective view of an in vitro training device of a preferred embodiment according to the present invention.

With reference to FIG. 2 showing a preferred embodiment of an in vitro training device T capable of carrying out the above in vitro training method for improving sleep apnea. The in vitro training device T includes an electrode patch 1 and an electrical stimulation module 2 in electrical connection with the electrode patch 1.

With reference to FIGS. 1 and 2, the electrode patch 1 has excellent electrical conductivity and softness to assure that the electrode patch 1 can be firmly adhered to the skin of the user and is less likely to peel off. Specifically, the electrode patch 1 includes a body surface adhering face 1a configured to be adhered to a bottom of a chin of the user. Thus, the electrode patch 1 can remain in a position aligned with the genioglossus muscle M of the user. Preferably, the body surface adhering face 1a can be repeatedly adhered to and removed from the skin of the user, such that the user can repeatedly use the same electrode patch 1, thereby increasing the use efficiency of material. The electrode patch 1 may include at least one electrical conductive portion 11 located on the body surface adhering face 1*a*. The electrical conductive portion 11 may contact with the skin of the user to proceed with in vitro electrical stimulation on the user.

The electrical stimulation module 2 is in electrical connection with the electrode patch 1 and can be controlled to send an electrical stimulation signal (with a predetermined voltage, a predetermined electric current, a predetermined frequency, and a predetermined pulse duration) to the electrode patch 1. Therefore, the user's genioglossus muscle M can be stimulated by in vitro transdermal electrical stimulation through the electrode patch 1. The present invention is not limited to the type of electrical connection between the electrical stimulation module 2 and the electrode patch 1. Namely, the electrical stimulation module 2 may be electrically connected to the electrode patch 1 via plural wires. Alternatively, as shown in the figures illustrating this embodiment, the electrode patch 1 may include an assembling face 1*b* opposite to the body surface adhering face 1*a* and configured to assemble with and position the electrical stimulation module 2. Thus, the electrical stimulation module 2 may be directly connected to the electrode patch 1 to form an electrical connection, such that no wires are required between the electrical stimulation module 2 and the electrode patch 1 for the electrical connection. Thus, the whole device can be more compact and tidy and is easier to use and carry.

The electrical stimulation module 2 is preferably detachably assembled with the assembling face 1*b* of the electrode patch 1. Thus, the electrode patch 1 can be replaced when the electrode patch 1 is damaged or malfunctions or the body surface adhering face 1*a* becomes not sticky enough. For example, the assembling face 1*b* of the electrode patch 1 may include at least one first electrical connecting portion 12. The electrical stimulation module 2 may include a casing 21, at least one power source 22 disposed in the casing 21, and at least one second electrical connecting portion 23 in electrical connection with the at least one power source 22 and located outside of the casing 21. The electrical stimulation module 2 may be rapidly coupled with the electrode patch 1 via magnetic attraction, such that the casing 21 covers a portion of the assembling face 1*b*, and the at least one second electrical connecting portion 23 is in electrical connection with the at least one first electrical connecting portion 12. The at least one power source 22 of the electrical stimulation module 2 may be replaced. Alternatively, the electrical stimulation module 2 may include a charging portion 24 for charging the at least one power source 22, or the at least one power source 22 may be charged wirelessly. The present invention is not limited in this regard.

Figure 3:
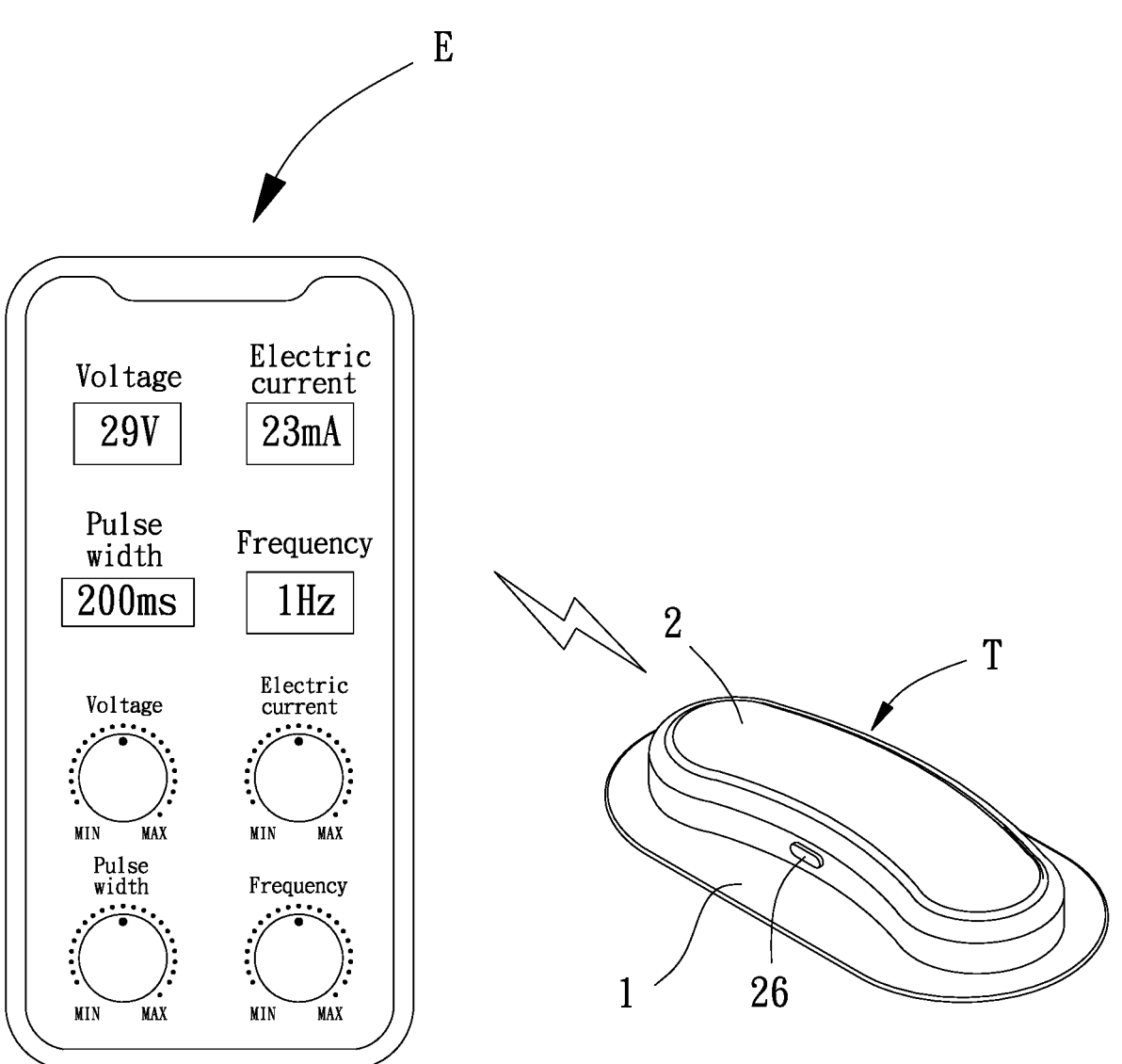
FIG. 3 is a schematic view illustrating coupling between the in vitro training device according to the present invention and an intelligent device.

With reference to FIGS. 2 and 3, the electrical stimulation module 2 may further include a control unit 25 located in the casing 21. The at least one power source 22 may also be in electrical connection with the control unit 25 to provide electricity to the control unit 25. Furthermore, the electrical stimulation module 2 may include a switch 26 disposed on the casing 21 for controlling power supply from the at least one power source 22 to the control unit 25. The control unit 25 can control the electrical stimulation signal sent to the electrode patch 1 and may be coupled with an intelligent device E, such as a mobile phone, a tablet, or a smart watch, which permits the user to proceed with personalized setting through an application interface of the intelligent device E according to the user's needs and comfort, thereby adjusting the stimulation intensity and/or the frequency of the electrical stimulation signal to improve the training effect and the training experience. For example, the voltage adjustment range may be 0-100 V, the electric current adjustment range may be 0-30 mA, the pulse width adjustment range may be 1-500 ms, and the frequency adjustment range may be 1-80 Hz. Thus, the user may start, adjust, pause, or stop the electrical stimulation according to needs.

Figure 4:
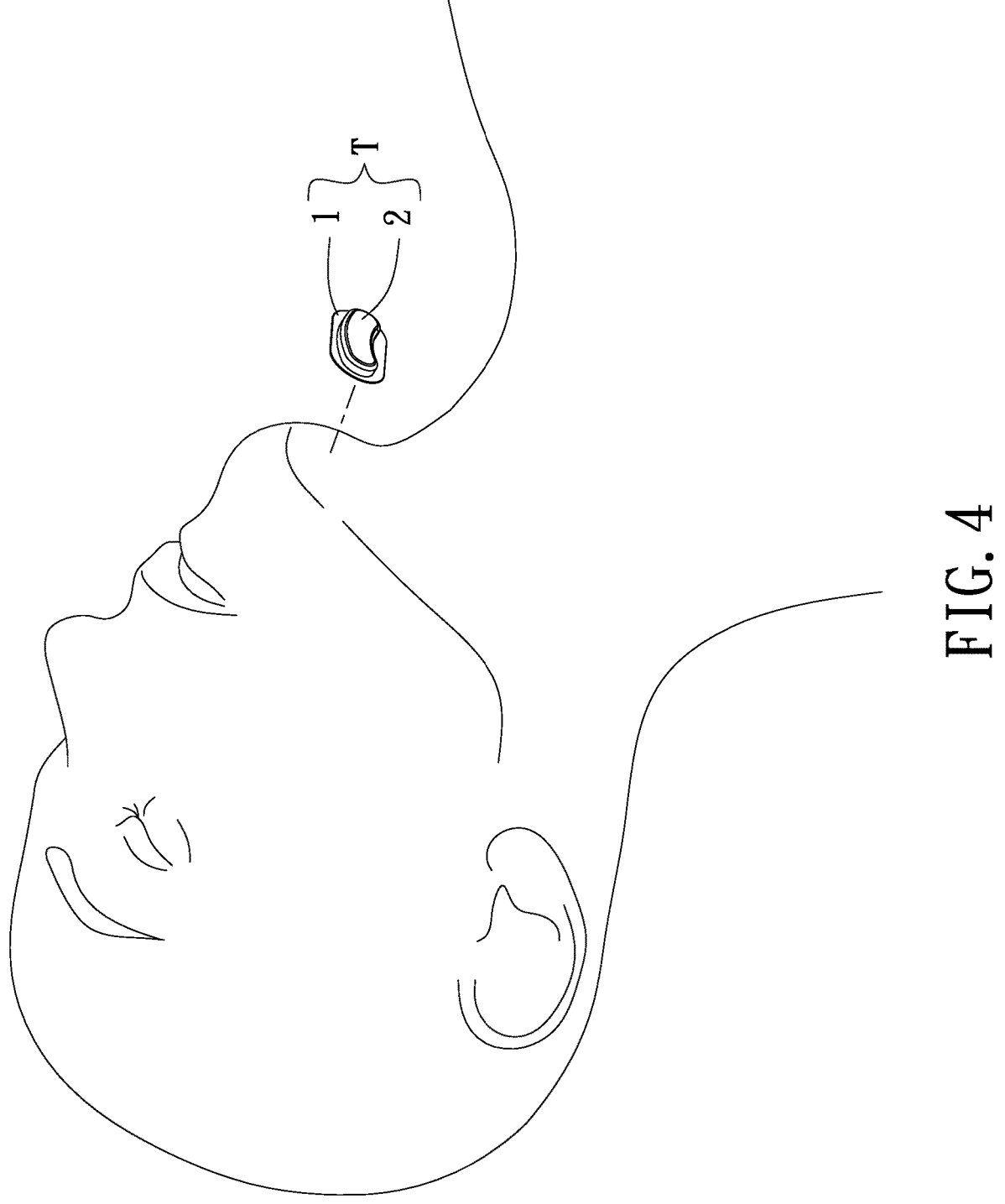
FIG. 4 is a schematic view illustrating use of the in vitro training device according to the present invention.

With reference to FIGS. 2-4, the user can use the in vitro training device T of this embodiment during the non-sleep period. In use, the electrode patch 1 is firstly adhered to the bottom of the chin of the user by the body surface adhering face 1*a* of the electrode patch 1, and the casing 21 of the electrical stimulation module 2 is coupled with the assembling face 1*b* of the electrode patch 1. Then, the switch 26 is pressed to activate the electrical stimulation module 2 to directly start the electrical stimulation. Alternatively, the electrical stimulation module 2 is in a standby state and can be operated through the application interface of the intelligent device E to start, pause, or set the time of electrical stimulation. Thus, the electrical stimulation of the present invention is not conducted during the sleep period, which not only prevents adverse effect on the sleep quality of the user but also permits the user to choose any time convenient to the electrical stimulation training in daily life, which can effectively increase the training convenience and comfort for the user to thereby increase the user's intention of continuous use. Furthermore, the in vitro training method of the present invention is not invasive and, thus, requires no devices to be implanted in the operation. This avoids the risks and inconvenience caused by the operational procedure and significantly reduces the burden to the user caused by the training.

In summary, the in vitro training method and the in vitro training device for training genioglossus muscle strength according to the present invention include the following advantages:

(1) No adverse effect on the sleep quality: The electrical stimulation of the present invention is not carried out during the sleep period and, therefore, will not cause discomfort during the sleep period, thereby avoiding adversely effect on the sleep quality of the user.

(2) Increasing the intention of continuous use: The user may proceed with the electrical stimulation training at any convenient time and place in daily life, which can effectively increase the training convenience and comfort for the user, thereby increasing the user's intention of continuous use.

(3) No operational risks: The in vitro training method of the present invention is not invasive and requires no devices to be implanted in the operation. This avoids the risks and inconvenience caused by the operational procedure and significantly reduces the burden to the user caused by the training.

(4) Easy to use and carry: The in vitro training device of the present invention is compact and very easy to carry. By contrast, CPAP can only be used near the equipment, and many cable ties and pipelines are disposed around the head of the user. The pipelines may even cause indentations on the face of the user. The user may walk at will when using the in vitro training device. The problems of many cable ties and pipelines required in the conventional CPAP are avoided. Therefore, the present invention is easy to use and significantly increases the comfort during use.

(5) Reduction in the equipment investment costs: In comparison with the conventional trainings methods requiring an operation or use of an expensive CPAP, the in vitro training device of the present invention has a lower equipment investment cost, such that more medical institutes and clinics can provide corresponding training services. Furthermore, the user can purchase his or her personal in vitro training device under a light burden and can proceed with the electrical stimulation at any time. Furthermore, the in vitro training device of the present invention has a simple structure and provides effects of increased maintenance efficiency and reduced maintenance costs.

(6) Saving time or labor cost: Use of the in vitro training method or the in vitro training device of the present invention does not require the time for operation and recovery while reducing the demand in the medical staff for the operation or training services, thereby saving time and labor costs.

Although the present invention has been described with respect to the above preferred embodiments, these embodiments are not intended to restrict the present invention. Various changes and modifications on the above embodiments made by any person skilled in the art without departing from the spirit and scope of the present invention are still within the technical category protected by the present invention. Accordingly, the scope of the present invention shall include the literal meaning set forth in the appended claims and all changes which come within the range of equivalency of the claims. Furthermore, in a case that several of the above embodiments can be combined, the present invention includes the implementation of any combination.

What is claimed is:

1. A non-implantable training method for training genioglossus muscle strength, comprising:

adhering an electrode patch of a non-implantable training device to a bottom of a chin of a user during a non-sleep period, with the electrode patch receiving an electrical stimulation signal from an electrical stimulation module to stimulate a genioglossus muscle of the user through transdermal electrical stimulation, wherein the electrical stimulation signal has a voltage of 1-100 V, an electric current of 1-30 mA, a pulse width of 1-500 ms, and a frequency of 1-80 Hz;

wherein the non-implantable training method is carried out plural times daily, with an interval between successive training times being at least one hour.

* * * * *